United States Patent [19]
Albertini

[11] Patent Number: 5,482,837
[45] Date of Patent: Jan. 9, 1996

[54] METHODS OF IDENTIFYING LYMPHOCYTES WITH MUTATOR PHENOTYPES

[75] Inventor: Richard J. Albertini, Underhill Center, Vt.

[73] Assignee: University of Vermont, Burlington, Vt.

[21] Appl. No.: 182,416

[22] Filed: Jan. 14, 1994

[51] Int. Cl.⁶ .............................. C12Q 1/68; C12N 15/00
[52] U.S. Cl. ................. 435/6; 435/7.24; 435/15; 435/29; 435/172.1
[58] Field of Search ................ 435/6, 7.24, 29, 435/15, 172.1

[56] References Cited

U.S. PATENT DOCUMENTS

| | | | |
|---|---|---|---|
| 4,066,510 | 1/1978 | Thilly | 435/6 |
| 4,544,632 | 10/1985 | Yamamura et al. | 435/948 |
| 4,647,535 | 3/1987 | Ritts, Jr. | 435/948 |
| 5,112,735 | 5/1992 | Albertini | 435/6 |

FOREIGN PATENT DOCUMENTS

WO88/10314  12/1988  WIPO.

OTHER PUBLICATIONS

Albertini et al., "T–Cell cloning to detect the mutant 6–thioguanine–resistant lymphocytes present in human peripheral blood." *PNAS, USA* 79:6617–6621 (1982).

Yanagi et al., "A human T cell–specific cDNA clone encodes a protein having extensive homology to immunoglobulin chains." *Nature* 308:145–148 (1984).

Yang et al., "Molecular evidence for new mutation at the hprt locus in Lesch–Nyhan patients." *Nature* 310:412–414 (1984).

Albertini et al., "Alterations of the hprt gene in human in–vivo–derived 6–thioguanine–resistant T lymphocytes." *Nature* 316:369–371 (1985).

Nicklas, J. et al., "Use of T-cell receptor gene probes to quantify the in vivo Hprt mutations in human T–lymphocytes." *Mutation Res.* 173:67–72 (1986).

Steen, A., et al., "hprt activities and RNA phenotypes in 6–thioguanine resistant human T–lymphocytes." *Mutation Res.* 286:209–15 (1993).

Sege–Peterson, K.; et al., "Characterization of mutation in phenotype variants of hypoxanthine phosphoribosyltransferase deficiency." *Human Molecular Genetics.* vol. 1(6):427–432 (1992).

Albertini et al, Environmental and Molecular Mutagenesis, vol. 21, Suppl. 22, p. 2, 1993.

Albertini et al, Environmental Health Perspectives, 99, 135–141, 1993.

Nicklas et al, Mutation Research, 215, 147–160, 1989.

Albertini et al, Annual Reviews of Genetics, 24, 305–326, 1990.

Primary Examiner—David Saunders
Attorney, Agent, or Firm—Campbell and Flores

[57] ABSTRACT

This invention provides methods for identifying lymphocytes with a mutator phenotype by isolating lymphocytes bearing a selectable marker; identifying among the lymphocytes a population belonging to the same clonally amplified set; and determining whether the population has at least two lymphocytes having, between them, two independent mutations among different alleles at the gene locus of the selectable marker; the presence of which indicates a mutator phenotype. In one embodiment of the invention, the selectable marker is hprt⁻.

4 Claims, No Drawings

METHODS OF IDENTIFYING LYMPHOCYTES WITH MUTATOR PHENOTYPES

BACKGROUND OF THE INVENTION

This invention was made with government support under ER 60502 awarded by the Department of Energy and CA 30688, awarded by the National Cancer Institute. The government has certain rights in the invention.

This invention relates generally to the field of molecular genetics and, more particularly, to methods of detecting proclivity to pathologies resulting from somatic cell mutation.

Mutations are alterations in chemical structure of DNA, the molecule that contains genetic information. While mutations are constantly being introduced into the DNA of dividing cells, cells possess the means, such as DNA repair enzymes, to correct mutations before they are passed on to progeny cells. Nevertheless, the correction mechanism is not perfect and mutations are introduced into mammalian somatic cells at rates of about $10^{-7}$ to about $10^{-6}$ per gene locus per cell generation.

Somatic mutational diseases result from cells bearing a mutation that was inherited or that arose spontaneously and that exists in the progeny of certain somatic cells. One example is cancer.

Many cancer causing agents, such as ultraviolet rays in sunlight and certain chemical compounds, are known to cause genetic mutations. In studying the link between genetic mutations and cancer, scientists identified oncogenes and tumor suppressor genes. When oncogenes are mutated, they can transform a normal cell into a cancer cell. While mutations in oncogenes may not be the only genetic cause of cancer, they do provide a causal link between a genetic event and a disease state.

These facts imply that individuals with faulty DNA repair mechanisms might be more prone to mutations and, therefore, to cancer than normal individuals. This is supported by the discovery of two diseases apparently involving deficiencies in DNA repair mechanisms: xeroderma pigmentosum and ataxia telangiectasia. Individuals with the former disease are subject to a very high incidence of sunlight-induced skin cancer. These individuals are deficient in enzymes repairing the type of damage done to DNA by ultraviolet light. Individuals with the latter disease are subject to an increased risk of breast cancer and appear to have deficiencies in enzymes that influence repair of breaks in the DNA chain.

Thus, there has been a long felt need for methods of identifying individuals who are prone to increased rates of mutation and, therefore, are at higher risk of somatic mutational diseases. Such methods would help doctors prevent such diseases, for example by warning patients to avoid carcinogenic agents, or treat diseases, by alerting doctors to screen for the disease so that it can be found in its early stages, when treatment is likely to be more effective.

There thus exists a need for methods for identifying individuals with a high rate of somatic cell mutation. This invention satisfies this need and provides related advantages as well.

SUMMARY OF THE INVENTION

This invention provides methods for identifying lymphocytes with a mutator phenotype by isolating lymphocytes bearing a selectable marker, identifying among the lymphocytes a population belonging to the same clonally amplified set, and determining whether the population has at least two lymphocytes having, between them, two independent mutations among different alleles at the gene locus of the selectable marker, the presence of which indicates a mutator phenotype. In one embodiment of the invention, the selectable marker is hprt$^-$.

According to another embodiment of the invention, the method involves isolating at least two groups of lymphocytes, each group bearing a different selectable marker, and determining whether any two groups contain a cell from the same clonally amplified set, the presence of which indicates a mutator phenotype.

DETAILED DESCRIPTION OF THE INVENTION

This invention provides methods for identifying individuals having lymphocytes with a "mutator phenotype." Cells exhibiting the mutator phenotype can have spontaneous mutation rates significantly higher than normal. While the normal mutation rate is about $10^{-7}$ to $10^{-6}$ per gene locus per generation, cells with a mutator phenotype can have mutation rates of greater than about $10^{-5}$ per gene locus per generation, more than ten times greater than normal. Also, these cells can be more susceptible than normal to certain mutagens or carcinogens. Both of these conditions are reflected as increases in mutant frequencies determined in a sample of the cells.

Genetic mutations are a cause of somatic mutational diseases, such as cancer. Therefore, individuals having lymphocytes with mutator phenotypes have greater-than-normal risk of developing somatic mutational diseases in these lymphocytes and other somatic cells as well.

According to a method of this invention, lymphocytes with a mutator phenotype are identified by isolating lymphocytes bearing a selectable marker, identifying among the lymphocytes a population belonging to the same clonally amplified set, and determining whether the population has at least two lymphocytes having, between them, two independent mutations among different alleles at the gene locus of the selectable marker. The presence of two or more independent mutations detected in a population from a clonally amplified set is evidence of a spontaneous mutation rate vastly in excess of $10^{-5}$ per gene locus per generation, or of an unusual hypersensitivity to a mutagen in the clone. Analysis of 25 to 100 representatives of the clonal population can suffice to identify the independent mutations.

In another embodiment of the invention, the method involves isolating at least two groups of lymphocytes, each group bearing a different selectable marker, and determining whether any two groups contain a cell from the same clonally amplified set. If so, this indicates the existence within the cells of a clonally amplified set of at least two, independent mutations. This shows a mutator phenotype.

The methods of this invention involve isolating lymphocytes bearing a selectable marker and identifying a population of the lymphocytes belonging to the same clonally amplified set. As used herein, "lymphocytes" refers to T-lymphocytes which carry T-cell receptors ("TCRs") or B-lymphocytes which produce antibodies. Any one lymphocyte produces only one type of TCR or antibody. Each TCR or antibody has specificity for one particular epitope, or antigen binding site, on its cognate antigen. Specific TCRs or antibodies are encoded by genes that are formed from the rearrangement of DNA in a lymphocyte stem cell that encodes the constant ("C"), joining ("J"), variable ("V") regions, and possibly diversity ("D") regions of the TCR or antibody. Mammals typically possess one-hundred thousand to one-hundred million lymphocytes of different specificities.

Upon stimulation of lymphocytes by an antigen, those lymphocytes specific for the antigen undergo clonal amplification. In this process the lymphocytes divide repeatedly in a "burst" of cell division, providing a large number of cells, called clones, produced from the same original parent cell and having specificity for the same epitope. This collection of cells is referred to herein as a "clonally amplified set."

Lymphocytes belonging to the same clonally amplified set are characterized at the genetic level by the possession of TCR or antibody genes having similarly rearranged structure that encode a TCR or an antibody specific for the same epitope. One method of detecting cells belonging to the same clonally amplified set is by determining the structure of the TCR or antibody genes. This can be done by analyzing restriction fragments of the genes by Southern blots, single strand conformation polymorphisms (SSCP), or by sequencing. Alternatively, but with more difficulty clonality can be determined by determining the structure of the proteins encoded by these genes and expressed by cells of the clone. Such methods are well known in the art.

A single clonally amplified set represents a small number of lymphocytes among the millions of lymphocytes in the body. Thus, members of the clonal population are identified from isolated lymphocytes bearing a gene conferring a selectable marker. As used herein, a "selectable marker" refers to any phenotypic trait of a lymphocyte that can be used to distinguish and isolate cells having the trait. The pool of lymphocytes bearing the same selectable marker will include lymphocytes belonging to a clonally amplified set. It also may include other lymphocytes that do not belong to the same set but that bear the marker. However, selecting cells that bear the marker will enrich the pool of lymphocytes for those belonging to a clonally amplified set and make their identification simpler.

In one embodiment of the invention, the selectable marker is resistance to a compound to which normal cells are susceptible. One such marker is resistance to 6-thioguanine, 8-azaguanine, 6-mercaptopurine or certain other purine analogues. This trait results from a mutation in the hprt gene. Cells having this selectable marker can be selected by exposing a collection of cells to any of these agents in a concentration sufficient to kill cells that do not have the marker. Thus, the pool will become enriched in cells having the marker.

In other embodiments of this invention the selectable marker is diphtheria resistance, ouabain resistance or loss of expression of a particular HLA sub-type. Cells having any of these markers can be selected by exposing a cell population to diphtheria toxin, ouabain or anti-HLA antibodies, respectively.

The indicator agent used for selection need not kill cells, as long as it provides a mechanism for distinguishing between wild-type and marked cells. For example, the indicator could potentially bind to cells of a certain phenotype, thereby allowing separation as by a cell sorter. For example, cells that have lost expression of an HLA subtype would fail to bind to a specific antibody to the HLA subtype, and may be distinguished by a cell sorter from cells that do so bind.

A method for identifying a lymphocyte population belonging to the same clonally amplified set and characterized by a selectable marker is described in Albertini, U.S. Pat. No. 5,112,735, incorporated herein by reference. The method involves the steps of obtaining a sample of lymphocytes from a mammal; cloning the lymphocytes in the presence of an agent indicative of a prior somatic mutation event at a gene locus in a lymphocyte to produce cloned cell populations; selecting those cloned cell populations that are indicated to have had the prior mutation event; growing the selected cloned cell populations separately to provide isolated mutated cloned cell populations; determining in the isolated, mutated, cloned cell populations the arrangement of the regions of the nucleic acid encoding an antigen receptor specific to a particular antigen; comparing the arrangement of the regions of the nucleic acid encoding an antigen receptor specific to a particular antigen among the isolated mutated cloned cell populations; and identifying cells undergoing amplification in response to a particular antigen stimulus, whereby the presence of a similar structure of the regions of nucleic acid encoding a specific antigen receptor in separate, isolated, mutated cell clones indicates clonal lymphocyte amplification in the mammal.

While not wishing to be bound by this explanation, it is believed that multiple mutations at a gene locus occur in the following manner and result in the following manifestations. At an early stage in clonal amplification, all the cells of the set are presumed to have the same alleles at a gene locus. During amplification a mutation is introduced into one of the cells. That cell passes the mutation on to its progeny. At this point, the set contains two types of cells with different alleles: cells with the original alleles and cells with alleles bearing the first mutation. Then, for example, a second mutation is introduced into one of the progeny of the cells bearing the original alleles. That cell passes the mutation onto its progeny. At this point, the set contains three types of cells with different alleles: cells with the original alleles, cells with alleles bearing the first mutation, and cells with alleles bearing the second mutation. Then, for example, a third mutation is introduced into one of the cells already bearing the first mutation. That cell passes on two mutations to its progeny. At this point, the set contains four types of cells with different alleles: cells with the original alleles, cells with alleles bearing the first mutation, cells with alleles bearing the second mutation and cells with alleles bearing the first and third mutations.

The presence of lymphocytes with two independent mutations among different alleles at a gene locus can be determined as follows. DNA from the cells in the population can be examined by, for example, Southern blot, for different restriction fragments of the gene. Alternatively, the copies of the gene from each cell in the population can be amplified by PCR, sequenced, and their nucleotide sequences compared. Both methods provide an indication of the structure of the genes. The latter method is, of course, more sensitive since it allows identification of every base in a gene. Then, the structure of the genes is compared between cells in the population.

While not wishing to be bound by the following explanation, it is believed that most mutator phenotypes result from a somatic cell mutations in genes regulating DNA repair. Individuals have many different gene loci for DNA repair enzymes. Because humans, and all other mammals, are diploid, they have two copies of each DNA-repair gene. In most individuals, both copies of the gene encode functional enzymes. However, some individuals are heterozygous and have inherited one functional copy of a DNA-repair gene and one non-functional copy. Since these individuals possess one functional copy of the gene, the presence of a defective gene normally will not lead to a defect in DNA repair. However, in certain cells of these heterozygous individuals the one functional gene copy may mutate and become non-functional. Such a cell no longer contains a functional DNA-repair enzyme encoded at this gene locus. Thus, these heterozygous individuals are, in reality, mosaics at the cellular level, having among the heterozygous cells a population of cells homozygous for a defect in DNA repair. Because these homozygous cells have decreased capacity to repair defects introduced into the DNA, they exhibit higher mutation rates or increased susceptibility to one or more environmental mutagens. Cells with increased mutation rates are, themselves, subject to increased risk of somatic mutational diseases, such as cancer. Furthermore, since the individual is heterozygous, other cells in the body are also at risk of becoming homozygous for a defect in DNA repair, resulting in higher mutation rates and increased risk of somatic mutational diseases in these cells, as well.

It is recognized that the change in a cell from heterozygosity to homozygosity for a defective DNA-repair enzyme is not the only way a cell can acquire a mutator phenotype. For example, a cell with functional DNA repair or "checkpoint" genes (genes that control the cell cycle) could develop a dominant mutation in one of them that impairs DNA repair activity by the cell. Or, a cell could develop a dominant mutation in one of the genes encoding a DNA polymerase gene, also rendering the cell subject to increased mutations. However, the mechanism of increased mutation is not critical. In all cases, an increased mutation rate over normal or an increased susceptibility to a mutagen puts the cell at risk of acquiring a somatic mutational disease.

The following example is meant to illustrate but not limit the invention.

EXAMPLE

Experimental results using T lymphocytes demonstrate the existence of both "normal" individuals who do not have a mutator phenotype and those who do have the mutator phenotype. The "normal" individual (renal transplant recipient) possessed an hprt⁻ population of T-lymphocytes belonging to the same clonally amplified set and having a mutation frequency of $919 \times 10^{-6}$. This frequency is more than 100-fold normal, presumably because of the renal transplantation. Twenty-five of 42 hprt⁻ mutant isolates were from the same TCR gene defined clonal set. Sequence analysis of 11 of these to date showed only a single hprt mutation. Therefore, there was no evidence of a mutator phenotype despite an enormous increase in mutant frequency.

The CD45 marker is expressed on T cells that have already undergone clonal expansion. It was found that T cells bearing CD45 had higher rates of mutation in the hprt gene than r cells that did not bear CD45 and, therefore, had not undergone clonal expansion. This is consistent with the hypothesis underlying this invention. The results are shown in Table I.

TABLE 1

Hprt MUTANT FREQUENCY IN CD45 SUBPOPULATIONS OF HUMAN T-LYMPHOCYTES

| Exp | Cell Population | $Mf \times 10^{-6}$ |
|---|---|---|
| Cl 169 | Unsorted | 11.6 |
|  | CD 45⁺ | 18.5 |
|  | CD 45⁻ | <1.2 |
| Cl 201 | Unsorted | 7.1 |
|  | CD 45⁺ | 54.0 |
|  | CD 45⁻ | 7.0 |

By contrast to the above, individuals were identified having a mutator phenotype. In one individual, 31 mutants from an hprt⁻ population of T lymphocytes belonging to the same clonally amplified set were sequenced. Four cells with different alleles at the gene locus were identified. Thirty mutants showed a deletion of exon 6 (due to $G_{485} \rightarrow T$ transversion in genomic DNA; a splice site mutation) in bp 485 and 1 showed a $T_{198} \rightarrow G$ transversion. However, and unexpectedly, two of the 30 with the exon 6 deletion showed a secondary exon 8 deletion (presumably splice site mutation) and one showed 2 extra frameshift mutations, +T after $G_{96}$ and +T after $G_{129}$. Two other hprt mutants that were not in the clonally amplified set showed a $C_{113} \rightarrow T$ transition and a $A_{581} \rightarrow T$ transversion. Also found were an additional 2-3 deletion mutations in an hprt mutant isolate from the clonally amplified set, in addition to the initial exon 6 splice site change. Also, in sequencing the Vβ TCR gene used in this clone, there was discovered a mutation resulting in a stop codon in the 5' targeted region of the Vβ gene. These secondary mutations indicate an enormous mutation rate in this clone.

Methods of molecular biology useful in the practice of this invention are known to the art or are described in Sambrook et al., Molecular Cloning, A Laboratory Manual, Cold Spring Harbor Laboratory, Cold Spring Harbor, N.Y. (1989).

Although the invention has been described with reference to the presently-preferred embodiments, it should be understood that various modifications can be made without departing from the spirit of the invention. Accordingly, the invention is limited only by the claims that follow.

I claim:

1. A method for identifying lymphocytes with a somatic mutator phenotype, comprising the steps of:
   a) isolating at least two groups of lymphocytes, each group bearing a different selectable marker; and
   b) determining whether any two groups contain a cell from the same clonally amplified set, the presence of which indicates the somatic mutator phenotype.

2. The method of claim 1 wherein the lymphocytes are T-lymphocytes.

3. The method of claim 2 wherein one of the selectable markers is hprt⁻.

4. The method of claim 2 wherein one of the selectable markers is diphtheria resistance, ouabain resistance or expression of a particular HLA sub-type.

* * * * *

UNITED STATES PATENT AND TRADEMARK OFFICE
CERTIFICATE OF CORRECTION

PATENT NO. : 5,482,837
DATED : January 9, 1996
INVENTOR(S) : Albertini, Richard J.

It is certified that error appears in the above-indentified patent and that said Letters Patent is hereby corrected as shown below:

In column 3, line 43, please delete the space between "6" and "-mercaptopurine"

In column 5, line 61, please delete "r cells" and replace therefor with --T cells--.

Signed and Sealed this

Fourth Day of March, 1997

Attest:

BRUCE LEHMAN

Attesting Officer

Commissioner of Patents and Trademarks